(12) United States Patent
Neumark et al.

(10) Patent No.: US 12,208,006 B2
(45) Date of Patent: Jan. 28, 2025

(54) CONSTRICTING A CARDIAC VALVE ANNULUS USING A CORD THAT HAS A LOOP PORTION AND A SINGLE SECOND PORTION

(71) Applicant: EDWARDS LIFESCIENCES CORPORATION, Irvine, CA (US)

(72) Inventors: David Neumark, Zichron Yaacov (IL); Nimrod Meller, Kfar Yehoshua (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 322 days.

(21) Appl. No.: 17/030,883

(22) Filed: Sep. 24, 2020

(65) Prior Publication Data
US 2021/0085461 A1     Mar. 25, 2021

Related U.S. Application Data (60) Provisional application No. 62/905,780, filed on Sep. 25, 2019.

(51) Int. Cl.
*A61F 2/24* (2006.01)

(52) U.S. Cl.
CPC .... *A61F 2/2445* (2013.01); *A61F 2220/0016* (2013.01); *A61F 2220/0075* (2013.01); *A61F 2250/001* (2013.01)

(58) Field of Classification Search
None
See application file for complete search history.

(56) References Cited

U.S. PATENT DOCUMENTS

| | | |
|---|---|---|
| 3,604,488 A | 9/1971 | Wishart et al. |
| 3,656,185 A | 4/1972 | Carpentier |
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |

(Continued)

FOREIGN PATENT DOCUMENTS

| | | |
|---|---|---|
| CN | 113331995 A | 9/2021 |
| EP | 1034753 A1 | 9/2000 |

(Continued)

OTHER PUBLICATIONS

International Search Report and Written Opinion issued in application No. PCT/US2020/052438 dated Jan. 12, 2021.

(Continued)

*Primary Examiner* — Megan Y Wolf (57) ABSTRACT

An enlarged cardiac valve annulus can be reduced in diameter using a cord that is affixed to the annulus by a set of anchors. A knot or fixed loop is disposed at a first end of the cord, and the body of the cord passes through the knot or fixed loop so as to form (a) a loop portion positioned distally beyond the knot or fixed loop and (b) a second portion that runs between the knot or fixed loop and the second end. The body of the cord can slide with respect to the knot or fixed loop. After the anchors are implanted and a bond between the anchors and the annulus is sufficiently strong, pulling the second portion in a proximal direction while holding the knot or fixed loop in place will reduce the circumference of the annulus.

16 Claims, 4 Drawing Sheets

(56) References Cited

U.S. PATENT DOCUMENTS

| | | |
|---|---|---|
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |

(56) References Cited

U.S. PATENT DOCUMENTS

| | | |
|---|---|---|
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |

(56) References Cited

U.S. PATENT DOCUMENTS

| | | |
|---|---|---|
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| RE46,126 E | 8/2016 | Kirson |
| RE46,127 E | 8/2016 | Kirson |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,517,130 B1 | 12/2016 | Alon et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,143,553 B2 | 12/2018 | Alon et al. |
| 10,206,776 B2 | 2/2019 | Alon |
| 10,357,364 B2 | 7/2019 | Alon |
| 10,368,852 B2 | 8/2019 | Gerhardt et al. |
| 10,398,555 B2 | 9/2019 | Alon et al. |
| 10,575,952 B2 | 3/2020 | Alon |
| 10,667,913 B2 | 6/2020 | Alon et al. |
| 10,695,179 B2 | 6/2020 | Alon |
| 10,716,670 B2 | 7/2020 | Alon |
| 10,786,356 B2 | 9/2020 | Alon |
| 10,881,390 B2 | 1/2021 | Modesitt et al. |
| 10,893,940 B2 | 1/2021 | Alon et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0093148 A1 | 5/2003 | Bolling et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0167062 A1 | 9/2003 | Gambale et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0049211 A1 | 3/2004 | Tremulis et al. |
| 2004/0059413 A1 | 3/2004 | Argento |
| 2004/0068273 A1 | 4/2004 | Fariss et al. |
| 2004/0106950 A1 | 6/2004 | Grafton et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |

(56) References Cited

U.S. PATENT DOCUMENTS

| | | |
|---|---|---|
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075654 A1 | 4/2005 | Kelleher |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0251177 A1 | 11/2005 | Saadat et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1* | 3/2007 | Douk ............... A61B 17/0401 128/897 |
| 2007/0055206 A1 | 3/2007 | To et al. |
| 2007/0060922 A1 | 3/2007 | Dreyfuss |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0033460 A1 | 2/2008 | Ziniti et al. |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |

(56) References Cited

U.S. PATENT DOCUMENTS

| | | |
|---|---|---|
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130965 A1* | 5/2010 | Sibbitt, Jr. ............ A61B 17/10 606/139 |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0053642 A1 | 3/2012 | Lozier et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245602 A1* | 9/2012 | Glick ............... B29C 65/5071 606/228 |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |

(56) References Cited

U.S. PATENT DOCUMENTS

| | | |
|---|---|---|
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0218206 A1 | 8/2013 | Gadlage |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163615 A1 | 6/2014 | Gadlage et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0030034 A1 | 2/2016 | Graul et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0120647 A1* | 5/2016 | Rogers ............ A61B 17/00234 606/139 |
| 2016/0135953 A1 | 5/2016 | Alon et al. |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0256274 A1 | 9/2016 | Hayoz |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0346084 A1 | 12/2016 | Taylor et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0071094 A1 | 3/2018 | Alon |
| 2018/0071095 A1 | 3/2018 | Alon et al. |
| 2018/0133009 A1 | 5/2018 | Alon |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0053905 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0201198 A1 | 7/2019 | Modesitt |
| 2019/0201199 A1 | 7/2019 | Modesitt |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015810 A1 | 1/2020 | Piccirillo |
| 2020/0015971 A1 | 1/2020 | Brauon et al. |
| 2020/0093622 A1* | 3/2020 | Nolan ..................... A61F 2/95 |
| 2020/0155316 A1 | 5/2020 | Alon |
| 2020/0163769 A1 | 5/2020 | Alon |
| 2020/0178956 A1 | 6/2020 | Mitelberg et al. |
| 2020/0229926 A1 | 7/2020 | Alon |
| 2020/0289267 A1 | 9/2020 | Peleg et al. |
| 2020/0337840 A1 | 10/2020 | Reich |
| 2021/0015475 A1 | 1/2021 | Lau |
| 2021/0052387 A1 | 2/2021 | Greenan et al. |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |
| 2023/0218291 A1 | 7/2023 | Zarbatany et al. |
| 2023/0320856 A1 | 10/2023 | Zarbatany et al. |
| 2024/0099736 A1 | 3/2024 | Elsheikh et al. |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A2 | 10/2002 |

(56) References Cited

FOREIGN PATENT DOCUMENTS

| | | |
|---|---|---|
| WO | 03047467 A1 | 6/2003 |
| WO | 2005046488 A2 | 5/2005 |
| WO | 2007098512 A1 | 9/2007 |
| WO | 2010000454 A1 | 1/2010 |
| WO | 2012176195 A2 | 12/2012 |
| WO | 2013088327 A1 | 6/2013 |
| WO | 2014064964 A1 | 5/2014 |
| WO | 2014195786 A2 | 12/2014 |
| WO | 2017204848 A1 | 11/2017 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Agarwal et al. International Cardiology Perspective Functional Tricuspid Regurgitation, Circ Cardiovasc Interv 2009;2;2;565-573 (2009).
Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.
Ahmadi, Ali et al. "Percutaneously adjustable pulmonary artery band." The Annals of thoracic surgery 60 (1995): S520-S522.
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri et al."Novel Suture Device for Beating-Heart Mitral Leaflet Approximation", Ann Thorac Surg. 2002, 74:1488-1493.
Alfieri, "The edge-to-edge repair of the mitral valve," [Abstract] 6th Annual NewEra Cardiac Care: Innovation & Technology, Heart Surgery Forum pp. 103. (2000).
Amplatzer Cardiac Plug brochure (English pages), AGA Medical Corporation (Plymouth, MN) (copyright 2008-2010, downloaded Jan. 11, 2011).
AMPLATZER® Cribriform Occluder. A patient guide to Percutaneous, Transcatheter, Atrial Septal Defect Closuer, AGA Medical Corporation, Apr. 2008.
AMPLATZER® Septal Occluder. A patient guide to the Non-Surgical Closuer of the Atrial Septal Defect Using the AMPLATZER Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success- midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. Ring+String, Successful Repair technique for ischemic mitral regurgitation with severe leaflet Tethering, The Department of Thoracic Cardiovascular surgery, Hamburg, Germany, Nov. 2008.
Maisano, The double-orifice technique as a standardized approach to treat mitral . . . , European Journal of Cardio-thoracic Surgery 17 (2000) 201-205.
Odell JA et al., "Early Results 04yf a Simplified Method of Mitral Valve Annuloplasty," Circulation 92:150-154 (1995).
O'Reilly S et al., "Heart valve surgery pushes the envelope," Medtech Insight 8(3): 73, 99-108 (2006).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976; 14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

\* cited by examiner

CONSTRICTING A CARDIAC VALVE ANNULUS USING A CORD THAT HAS A LOOP PORTION AND A SINGLE SECOND PORTION

CROSS REFERENCE TO RELATED APPLICATIONS

This application claims the benefit of U.S. Provisional Application 62/905,780, filed Sep. 25, 2019, which is incorporated herein by reference in its entirety.

BACKGROUND

Figure 1:
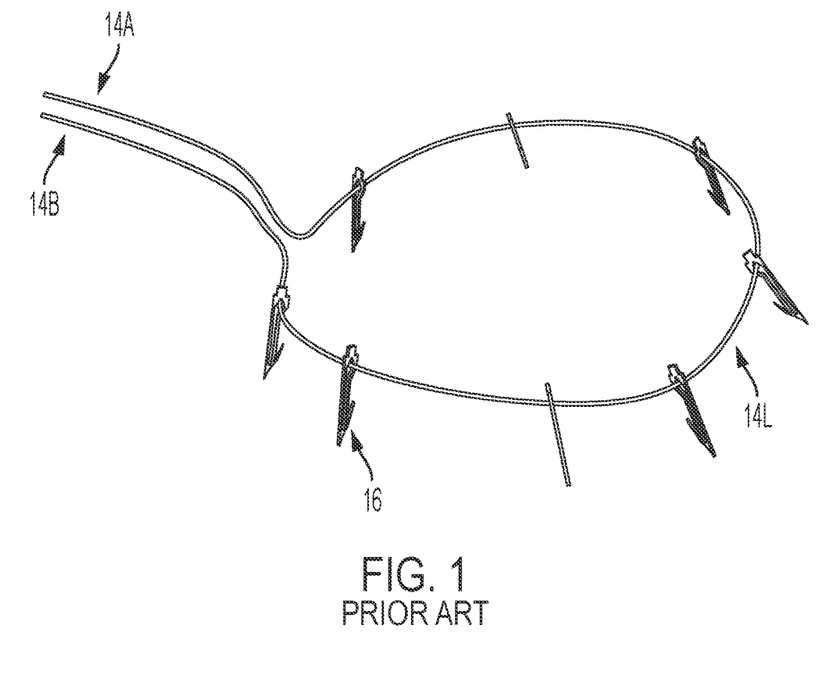
FIG. 1 depicts a prior art annulus-constricting implant.

Our prior applications WO 2013/088327 and WO 2014/195786, which are incorporated herein by reference, describe affixing a cord to an annulus of a cardiac valve and subsequently using that cord to reduce the diameter the annulus. FIG. 1 depicts a prior art approach in which a cord is affixed to a cardiac valve annulus (or adjacent leaflets) using a set of anchors 16. The cord includes a distal section 14L that initially conforms to the shape of the enlarged annulus, and two proximal sections 14A and 14B of the cord extend from the ends of the loop section 14L through the subject's vasculature to an access port. After the anchors 16 are driven into the annulus or leaflet tissue and a sufficiently strong bond has formed between the tissue and the anchors (which can take 4-8 weeks), a push tube is advanced through the subject's vasculature over the two proximal sections 14A and 14B until the distal end of the push tube reaches the ends of the loop section 14L. At this point, pulling the two proximal sections 14A and 14B of the cord in a proximal direction while pushing the push tube in a distal direction will cause the annulus to contract. The two proximal sections 14A and 14B are then fastened together right next to the loop section to hold the annulus in its new contracted state, and the portions of sections 14A and 14B that are proximal to the fastener are then cut off and removed (e.g., as described in US 2019/0201198).

SUMMARY OF THE INVENTION

This application describes alternative approaches for reducing the diameter of an annulus of a cardiac valve.

One aspect of the invention is directed to a first apparatus for resizing an annulus of a cardiac valve. The annulus has an initial circumference. The first apparatus comprises a cord and at least four anchors. The cord has a first end, a second end, a body that runs between the first end and the second end, and a knot or fixed loop disposed at the first end of the cord. The body of the cord passes through the knot or fixed loop so as to form (a) a loop portion positioned distally beyond the knot or fixed loop and (b) a second portion that runs between the knot or fixed loop and the second end. And the knot or fixed loop is configured so that the body of the cord can slide with respect to the knot or fixed loop. The at least four anchors are distributed about the loop portion, and each of the at least four anchors is configured for implantation into the annulus or adjacent tissue so that immediately subsequent to implantation the anchor will hold a respective part of the loop portion adjacent to the annulus. Preferably, each of the at least four anchors is also configured to (a) resist extraction immediately subsequent to implantation and (b) develop, over time, a bond with the annulus or adjacent tissue that is sufficiently strong such that pulling the second portion in a proximal direction while holding the knot or fixed loop in place will reduce the circumference of the annulus.

Some embodiments of the first apparatus further comprise a sleeve of material that accepts tissue ingrowth disposed over the loop portion. Optionally, in these embodiments, each of the at least four anchors holds the respective part of the loop portion adjacent to the annulus by holding a corresponding part of the sleeve to the annulus.

In some embodiments of the first apparatus, there are at least eight anchors. In some embodiments of the first apparatus, the knot or fixed loop comprises a fixed loop that is secured by a surgeon's loop knot. In some embodiments of the first apparatus, the knot or fixed loop comprises a noose knot.

In some embodiments of the first apparatus, each of the at least four anchors includes a pointy front end and a back end, and a slot that runs in a front-to-back direction. Optionally, in these embodiments, the slot is a linear slot.

Some embodiments of the first apparatus further comprise a clip that is applied to the second portion adjacent to the knot or fixed loop subsequent to reduction in the circumference of the annulus. The clip is positioned to prevent the loop portion of the cord from expanding.

Another aspect of the invention is directed to a first method for resizing an annulus of a tricuspid valve. The annulus has an initial circumference. The first method comprises delivering a cord and at least six anchors to a vicinity of the annulus. The cord has a first end, a second end, a body that runs between the first end and the second end, and a knot or fixed loop disposed at the first end of the cord. The body of the cord passes through the knot or fixed loop so as to form (a) a loop portion that follows a contour of the annulus and is positioned distally beyond the knot or fixed loop and (b) a second portion that runs between the knot or fixed loop and the second end. The knot or fixed loop is configured so that the body of the cord can slide with respect to the knot or fixed loop. The at least six anchors are distributed about the loop portion. The first method also comprises implanting the at least six anchors into the annulus or adjacent tissue so that immediately subsequent to implantation, each of the anchors will hold a respective part of the loop portion adjacent to the annulus.

Some instances of the first method further comprise waiting for a bond to develop between the at least six anchors and the annulus or adjacent tissue. Subsequent to the development of the bond, the second portion is pulled in a proximal direction while holding the knot or fixed loop in place to reduce the circumference of the annulus. Subsequent to the pulling, the cord is fastened to prevent the annulus from expanding.

In some instances of the first method, the tricuspid valve has a septal leaflet, an anterior leaflet, and a posterior leaflet. The at least six anchors are distributed about the loop portion so that a first one of the anchors is closest to the knot or fixed loop and a last one of the anchors is furthest from the knot or fixed loop. In these instances, when the at least six anchors are implanted, (a) the first one of the anchors is implanted into the septal leaflet or into a portion of the annulus to which the septal leaflet is attached and (b) the last one of the anchors is implanted into the posterior leaflet or into a portion of the annulus to which the posterior leaflet is attached.

In some instances of the first method, the at least six anchors comprises at least nine anchors. In some instances of the first method, the knot or fixed loop comprises a fixed loop that is secured by a surgeon's loop knot. In some instances of the first method, the knot or fixed loop comprises a noose knot.

In some instances of the first method, each of the at least six anchors includes a pointy front end and a back end, and a slot that runs in a front-to-back direction. Optionally, in these instances, the slot is a linear slot.

In some instances of the first method, the fastening comprises affixing a clip to the second portion adjacent to the knot or fixed loop, and the clip is positioned to prevent the loop portion of the cord from expanding.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Although the FIG. 1 embodiment is effective, the fasteners and cutting system described in US 2019/0201198 are relatively complex because they must fasten and cut two proximal sections 14A, 14B. In contrast, the FIGS. 2-6 embodiments described below each operate using only a single proximal section of cord. This makes it possible to use less complicated fasteners and cutters, and can also provide significant additional advantages as described below.

Figure 2:
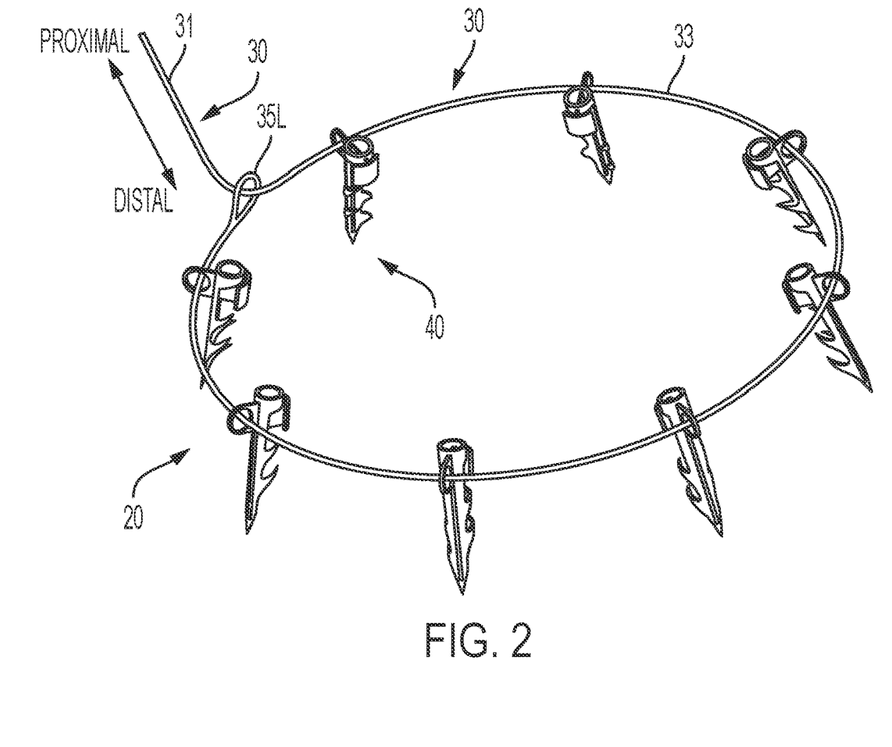
FIG. 2 depicts a first embodiment of an annulus-constricting implant that is configured for implantation into an annulus of a cardiac valve.

FIG. 2 depicts one embodiment of an annulus-constricting implant 20 that is designed for implantation into an annulus of a cardiac valve (e.g. the mitral valve annulus or the tricuspid valve annulus). The implant 20 may be implanted either directly into the annulus itself or into adjacent tissue (e.g., into the leaflets of the cardiac valve near the base of those leaflets). For example, when the implant is installed in the mitral valve, it may be installed directly into the mitral annulus via a catheter from the atrium side or into the leaflets via a catheter from the ventricle side. Note that these two alternative approaches for affixing implants to either the annulus or adjacent tissue are described in application WO 2014/195786 (in connection with an implant that has a different construction).

The implant 20 includes a cord 30 that has a first end and a second end. The body of the cord 30 runs between the first end and the second end. Note that as used herein, the term "cord" includes monofilament cords, multi-filament cords, braided cords, wires, and other cord-shaped flexible structures. Suitable materials for the cord include stainless steel, Dyneema, ultra high molecular weight polyethylene, LCP, Nylon, PET, Dacron, and other high-strength polymers, all of which are biocompatible and sufficiently strong to constrict the annulus. In some embodiments, the diameter of the cord 30 is between 0.2 and 0.4 mm. In some embodiments, the diameter of the cord 30 is between 0.2 and 0.8 mm.

A fixed loop 35L is disposed at the first end of the cord 30. As used herein, a fixed loop means a closed loop with a circumference that does not change. The fixed loop 35L may be formed using any of a variety of approaches that will be apparent to persons skilled in the relevant arts. For example, the fixed loop may be formed by tying a suitable knot (e.g., a surgeon's loop knot, a perfection knot, etc.) at the first end of the cord 30 to create the fixed loop. A wide variety of alternative knots that create a fixed loop at the first end of the cord 30 may also be used. In those embodiments that use a multi-filament cord 30, an eye splice may be used to form the fixed loop. In other embodiments, a separate metal loop (not shown) may be affixed to the first end of the cord 30. The fixed loop 35L is large enough so that the body of the cord 30 can slide through the fixed loop 35L without undue friction, and small enough to prevent the clip (described below in connection with FIG. 4) from slipping through the "eye" in the middle of the fixed loop 35L. In some embodiments, the area enclosed by the fixed loop 35L is less than 3× or less than 2× the cross-sectional area of the cord 30.

The body of the cord 30 passes through the fixed loop 35L so as to form (a) a loop portion 33 positioned distally beyond the fixed loop 35L and (b) a second portion 31 that runs between the fixed loop 35L and the second end. In some embodiments, when the implant 20 is initially implanted into the annulus or adjacent tissue, the circumference of the loop portion 33 matches the circumference of the annulus to which the implant will be attached. In other embodiments, when the implant 20 is initially implanted into the annulus or adjacent tissue, the circumference of the loop portion 33 is slightly larger than the circumference of the annulus to which the implant will be attached. In some embodiments, when the implant 20 is initially implanted into the annulus, the circumference of the loop portion 33 is between 125 and 220 mm. In some embodiments, when the implant 20 is initially implanted into the annulus, the circumference of the loop portion 33 is between 95 and 285 mm.

The fixed loop 35L is configured so that the body of the cord 30 can slide through the fixed loop 35L. It will be apparent from an inspection of FIG. 2 that when the cord 30 slides through the fixed loop 35L in the proximal direction (e.g., if the second portion 31 of the cord is pulled in the proximal direction while the fixed loop 35L is held in place), the circumference of the loop portion 33 of the cord 30 will get smaller, while the length of the second portion 31 of the cord 30 will simultaneously get longer.

The implant 20 includes at least four anchors 40 distributed around the loop portion 33 of the cord 30. Each of the at least four anchors is configured for implantation into the annulus or adjacent tissue so that immediately subsequent to implantation the anchor will hold a respective part of the loop portion 33 adjacent to the annulus. In the embodiments depicted herein, the implant 20 has eight anchors 40.

The anchors 40 are used to attach the implant 20 to the annulus or adjacent tissue. In some preferred embodiments, the anchors 40 may be constructed and connected to the cord 30 as described in U.S. Pat. No. 9,517,130, which is incorporated herein by reference in its entirety. And it is this approach that is illustrated in FIG. 2. Each of the anchors 40 has a pointy front end and a back end, and preferably has a slot 45 that runs in a front-to-back direction. This slot 45 is configured so that after the cord is brought into position adjacent to the annulus, the anchors can move with respect to the cord 30 and penetrate into the annulus or adjacent tissue. The slot 45 is preferably a linear slot.

Each of the at least four anchors 40 is configured for implantation into the annulus or adjacent tissue so that immediately subsequent to implantation the anchor will hold a respective part of the loop portion 33 adjacent to the annulus. The interconnection between the anchors 40 and the loop portion 33 may be direct (e.g. in embodiments where the cord 30 passes through the slot in each of the anchors, as depicted in FIG. 8 of U.S. Pat. No. 10,206,776, which is incorporated herein by reference in its entirety). Alternatively, the interconnection between the anchors 40 and the loop portion 33 may be indirect (e.g., in embodiments where the cord 30 is held in place by a sleeve, and the anchors are attached to the sleeve, as depicted in FIG. 56B of U.S. Pat. No. 10,206,776.)

Prior to deployment, the implant 20 is positioned up against the tissue into which it will be implanted, with the pointy front ends of the anchors 40 facing the tissue. During deployment, a set of anchor launchers drives the anchors 40 in a forward direction (e.g., using one anchor launcher per anchor 40). The pointy front end of the anchor 40 will be driven into the tissue and the barbs will become embedded into the tissue, which will affix the implant 20 to the tissue. Implantation of the anchors 40 may be accomplished using a variety of approaches, including but not limited to the anchor launchers described in U.S. Pat. No. 10,206,776.

The implant 20, including the anchors 40, may be delivered to the vicinity of the annulus using the delivery system described in U.S. application Ser. No. 15/699,604 (published as US 2018/0071094), which is incorporated herein by reference in its entirety.

After implantation of the implant 20 into the annulus or adjacent tissue, the delivery system that is used to deliver the implant 20 to the annulus is removed. At this stage, the anchors 40 hold the loop portion 33 of the cord to the annulus, and the second portion 31 of the cord 30 runs from the annulus through the patient's vasculature to an exit point (e.g., the right internal jugular vein).

Immediately after implantation of the anchors 40 into the annulus or adjacent tissue, each of the anchors will hold a respective part of the loop portion adjacent to the annulus, but the bond between the implant 20 and the annulus or adjacent tissue may not be sufficiently strong withstand tightening. But over time (e.g., 1-3 months after implantation), the bond between the anchors 40 and the annulus or adjacent tissue will become sufficiently to withstand tightening. While not being bound by this theory, it is believed that the increased strength of the bond over time is largely attributable to injury points that arise when the anchors 40 are implanted into the annulus or adjacent tissue. And the presence of slots 45 in the anchors 40 can be a significant contributing factor to obtaining a strong bond.

In some cases, the anchors 40 may be attached to the annulus or adjacent tissue with sufficient strength to withstand constriction immediately after the implant has been implanted, in which case the cord 30 may be constricted immediately after the implant is implanted. But in other cases, the attachment strength may not be sufficient to withstand constriction. In the latter situation (or when the practitioner does not know the strength of attachment), it could be dangerous to constrict the cord 30 immediately after implantation, because when the bond is not sufficiently strong, the constricting action could tear the implant away from the annulus. In these circumstances, it is preferable to wait until the bond between the anchors 40 and the annulus or adjacent tissue become sufficiently strong (e.g. by operation of the injury points and/or tissue ingrowth) to withstand tightening.

After a bond has developed between the implant 20 and the annulus or adjacent tissue that is sufficiently strong to withstand tightening, the implant is ready to be used to reduce the diameter of the annulus.

In some preferred embodiments, constriction of the diameter of the annulus is accomplished from outside the patient's body via a catheter, in which case the second portion 31 should be sufficiently long (e.g., 25-100 cm) to reach from the annulus to outside the patient's body via the patient's vasculature. Optionally, the proximal end of the cord 30 (i.e. the second end) may be wound up into a small pouch that is implanted just beneath the patient's skin during the time that the bond between the implant 20 and the annulus is growing stronger.

Figure 3:
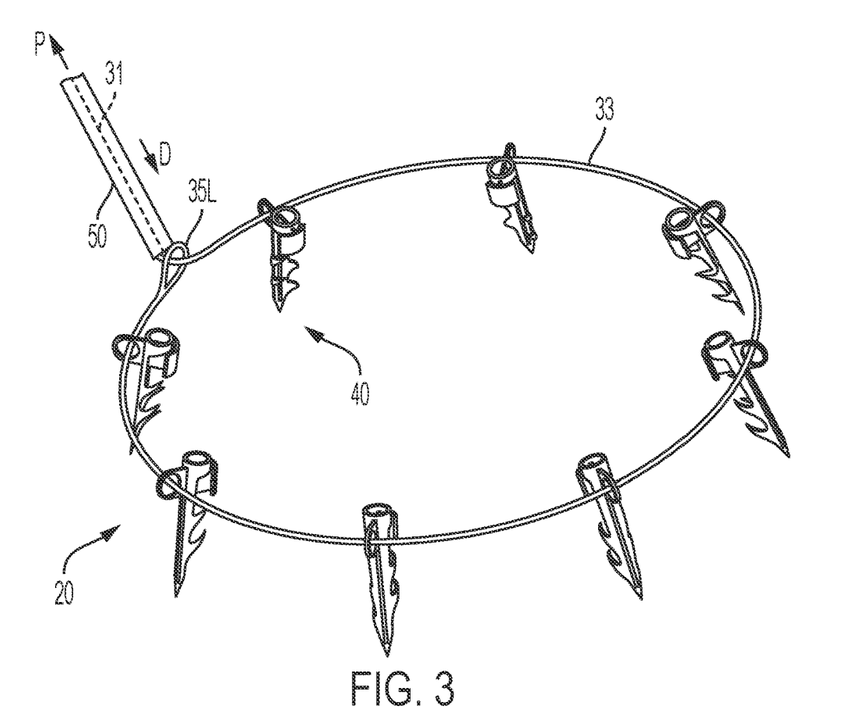
FIG. 3 depicts one approach for using the implant of FIG. 2 to reduce the diameter of the annulus.

FIG. 3 depicts one preferred approach for reducing the diameter of the annulus. In this approach, the practitioner slides a push-tube 50 down over the second portion 31 of the cord 30 until the distal end of the push tube 50 reaches the fixed loop 35L of the cord 30. Because the second portion 31 extends through the patient's vasculature between the implant 20 and an exit point, the second portion 31 can serve as a guide wire over which the push tube 50 can be guided to its destination. When the push tube 50 is in this position and is pushed in a distal direction (indicated by the arrow D), the push tube 50 will hold the fixed loop 35L in place. The second portion 31 of the cord 30 is then pulled in a proximal direction (indicated by the arrow P). The cord 30 will then slide through the fixed loop 35L in a direction that causes the circumference of the loop portion 33 to get smaller. And because the loop portion 33 of the cord 30 is strongly attached to the annulus or adjacent tissue by the anchors 40, the reduction in circumference of the loop portion 33 will reduce the diameter of the annulus.

Figure 4:
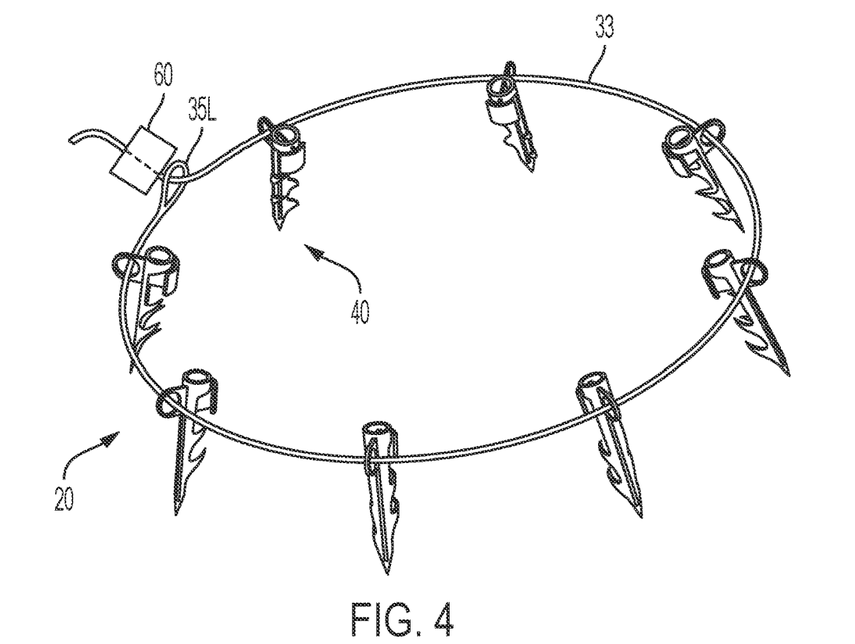
FIG. 4 depicts the FIG. 2 implant after a clip that prevents re-expansion of the annulus has been affixed to the cord.

After the diameter of the annulus has been reduced, subsequent re-expansion of the diameter of the annulus must be prevented by fastening the cord 30 so that the circumference of the loop portion 33 cannot increase. One approach for accomplishing this is to affix a clip 60 to the second portion 31 of the cord adjacent to the fixed loop 35L, as depicted in FIG. 4. Examples of clips that are suitable for this purpose and approaches for affixing those clips are described in U.S. application Ser. No. 16/234,804 (published as US 2019/0201198), which is incorporated herein by reference in its entirety. (The '804 application also describes methods and systems that combine the functionality of the push tube 50 depicted in FIG. 3 and the clip 60 depicted in FIG. 4.) When this approach is used, the clip should be large enough so that it cannot slip through the "eye" in the middle of the fixed loop 35L. After the clip 60 is attached to the second portion 31 of the cord adjacent to the fixed loop 35L, the portion of the cord that is proximal with respect to the clip 60 can be cut away. A variety of alternative approaches may also be used to prevent re-expansion of the annulus, including but not limited to attaching other structures that are too large to slip through the "eye" to the second portion 31 of the cord adjacent to the fixed loop, tying the second portion of the cord 31 to the fixed loop 35L using a knot, etc.

Figure 5:
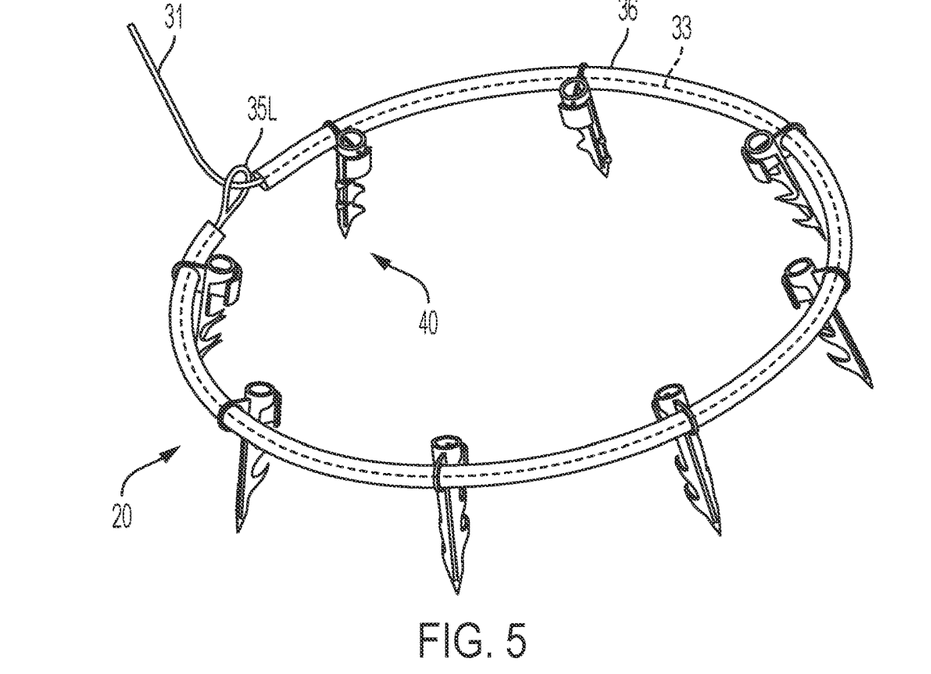
FIG. 5 depicts a second embodiment of an annulus-constricting implant.

The FIG. 5 embodiment is similar to the FIG. 2 embodiment, but adds an additional component. More specifically, in the FIG. 5 embodiment, the loop portion 33 is surrounded by a sleeve 36. The sleeve 36 may be made from a material that accepts tissue ingrowth, such as PET braid, Nylon braid, wool, silk, or non-woven polymers. As a result, after the implant 20 is implanted into the annulus or adjacent tissue, tissue that comes into contact with the implant 20 will slowly ingrow into the sleeve 36. This ingrowth can strengthen the bond between the implant 20 and the annulus or adjacent tissue. In the embodiment depicted in FIG. 5, the sleeve 36 is continuous and tubular, and runs the entire length of the loop portion 33. In alternative embodiments (not shown), two or more separate pieces of sleeving may be used instead of a continuous sleeve. For example, in a system having N anchors 40, a separate piece of tubular sleeving may be positioned between each of the N anchors 40, in which case N-1 separate pieces of sleeving would be used. In alternative embodiments, non-tubular sleeving may be used.

Optionally, a lining (not shown) that resists tissue ingrowth may be provided on the interior surface of the sleeve 36. This ingrowth-preventing lining helps the loop portion 33 slide freely within the sleeve 36 when constricting is eventually implemented, and helps prevent the loop portion 33 from becoming locked in place by the surrounding tissue due to tissue ingrowth. Suitable materials for the ingrowth-preventing lining on the interior surface of the sleeve 36 include Teflon and ePTFE.

Optionally, the loop portion 33 may be coated with a coating (not shown) that resists tissue ingrowth. The coating on the loop portion 33 prevents the tissue that grows into the implant from adhering to the loop portion 33, so that the loop portion 33 will be able to slide freely within the sleeve 36 when constricting is eventually implemented, and prevent the loop portion 33 from becoming locked in place by the surrounding tissue due to ingrowth. Suitable materials for the coating include Teflon and ePTFE.

Reduction of the diameter of the annulus in the FIG. 5 embodiment may be accomplished using the same approach described above in connection with FIG. 3. More specifically, when a similar push tube 50 is advanced over the second portion 31 of the cord so that the push tube 50 hold the fixed loop 35L in place, pulling the second portion 31 of the cord 30 in a proximal direction will cause the circumference of the loop portion 33 to get smaller, which will reduce the diameter of the annulus.

Fastening the cord 30 in the FIG. 5 embodiment may be accomplished using any of the approaches described above in connection with FIG. 4.

Figure 6:
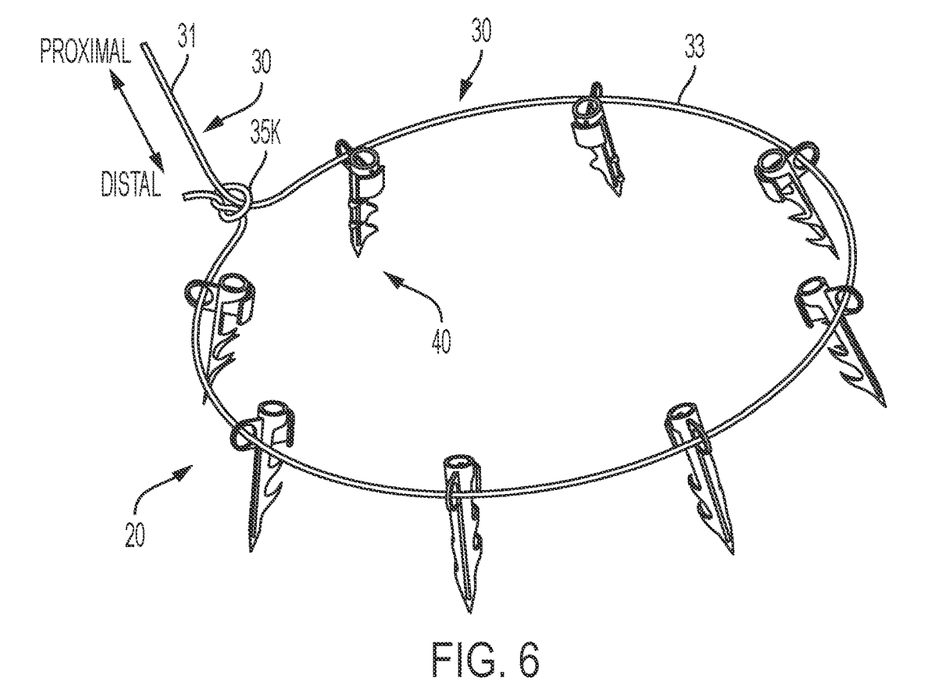
FIG. 6 depicts a third embodiment of an annulus-constricting implant.

FIG. 6 depicts another embodiment of an annulus-constricting implant 20 that is designed for implantation into an annulus of a cardiac valve or adjacent tissue. This embodiment is similar to the FIG. 2 embodiment in all respects, except that a knot 35K is used in the FIG. 6 embodiment in place of the fixed loop 35L described above in connection with the FIG. 2 embodiment.

The implant 20 includes a cord 30 that has a first end and a second end. The body of the cord 30 runs between the first end and the second end. A knot 35K is disposed at the first end of the cord 30. The knot is configured so that the body of the cord 30 can slide through the knot 35K without undue friction. One example of a knot that is suitable for this purpose is the noose knot (which is illustrated in FIG. 6), and a variety of alternative knots may also be used, as will be appreciated by persons skilled in the relevant arts.

The body of the cord 30 passes through the knot 35K so as to form (a) a loop portion 33 positioned distally beyond the knot 35K and (b) a second portion 31 that runs between the knot 35K and the second end. It will be apparent from an inspection of FIG. 6 that when the cord 30 slides through the knot 35K in the proximal direction (e.g., if the second portion 31 of the cord is pulled in the proximal direction while the knot 35K is held in place), the circumference of the loop portion 33 of the cord 30 will get smaller, while the length of the second portion 31 of the cord 30 will simultaneously get longer.

The implant 20 includes at least four anchors 40 distributed around the loop portion 33 of the cord 30, and each of the at least four anchors is configured to hold a respective part of the loop portion 33 adjacent to the annulus. The anchors 40; the interconnection between the anchors 40 and the loop portion 33; and the delivery, deployment, and implantation of the anchors 40 are all as described above in connection with the FIGS. 2-5 embodiment.

After a bond has developed between the implant anchors 40 and the annulus or adjacent tissue that is sufficiently strong to withstand tightening, the implant 20 is ready to be used to reduce the diameter of the annulus, and the same push-tube approach described above in connection with FIG. 3 may be used to tighten the FIG. 6 embodiment. More specifically, the practitioner slides a push-tube down over the second portion 31 of the cord 30 until the distal end of the push tube reaches the knot 35K of the cord 30. The second portion 31 of the cord 30 is then pulled in a proximal direction. The cord 30 will then slide through the knot 35K in a direction that causes the circumference of the loop portion 33 to get smaller. And because the loop portion 33 of the cord 30 is strongly attached to the annulus or adjacent tissue by the anchors 40, the reduction in circumference of the loop portion 33 will reduce the diameter of the annulus.

After the diameter of the annulus has been reduced, subsequent re-expansion of the diameter of the annulus is prevented using any of the approaches described above in connection with FIGS. 2-5. And the optional sleeve 36 depicted in FIG. 5 may also be used in this FIG. 6 embodiment.

Although the embodiments illustrated in FIGS. 2-6 each have eight anchors 40, a different number of anchors 40 may be used. In some preferred embodiments, a larger number of miniature anchors are used. For example, 20 anchors that are between 4 and 8 mm long may be used. In other alternative embodiments, 16 or more anchors are used (e.g., between 16 and 24); and in other alternative embodiments, 8 or more anchors are used. In the latter case, the anchors may be larger (e.g., between 6 and 12 mm long). It is expected that a minimum of four anchors is required to effectively affix the implant 20 onto the annulus.

Figure 7:
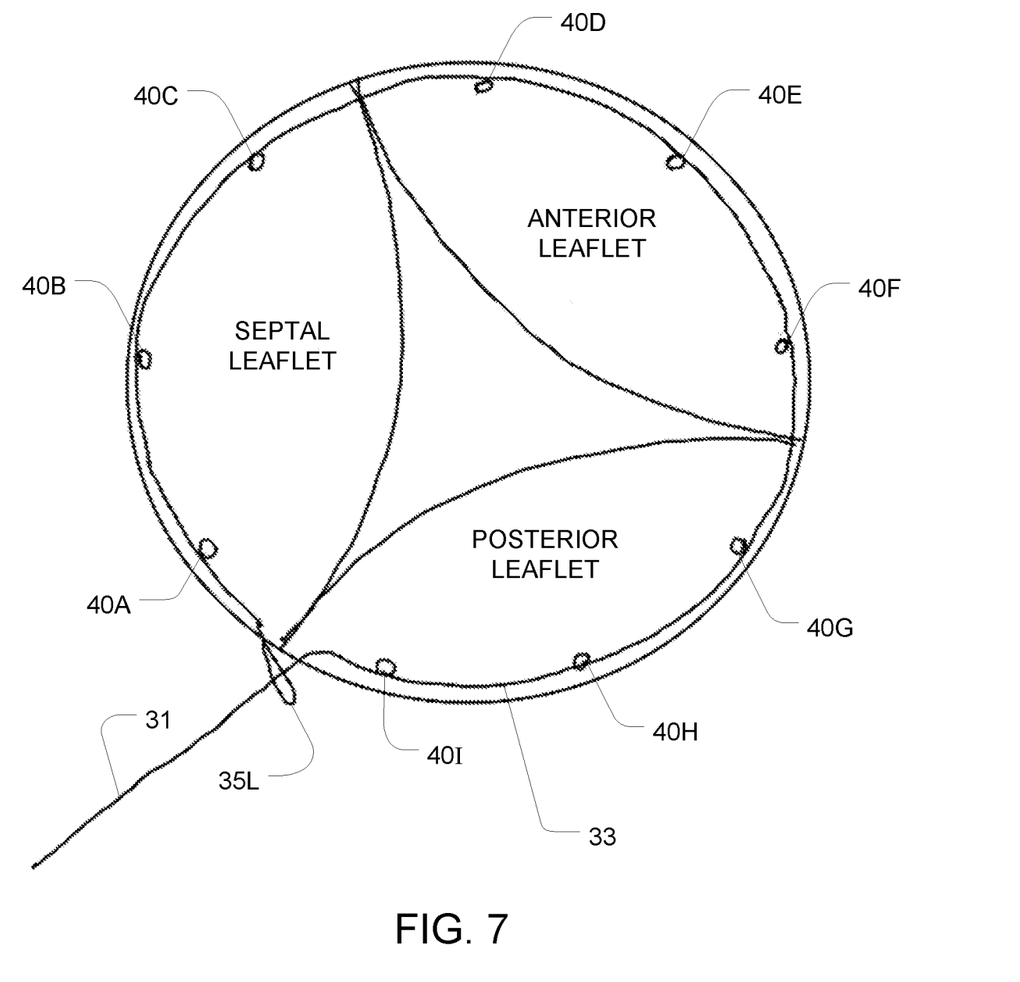
FIG. 7 depicts a preferred way to position and orient the FIG. 2-6 embodiments when those embodiments are used to reduce the diameter of a tricuspid valve annulus.

FIG. 7 depicts a plan view (as viewed from the right atrium side) of a preferred positioning and orientation when any of the embodiments described above in connection with FIG. 2-6 are used to reduce the diameter of a tricuspid valve annulus.

Assume that the tricuspid valve annulus has an initial circumference. A cord and at least six anchors 40A-40I are delivered to a vicinity of the annulus. Anchors similar to the anchors described above in connection with FIG. 2-6 may be used. For example, each of the anchors may include a pointy front end and a back end, and a slot (e.g., a linear slot) that runs in a front-to-back direction.

The cord has a first end, a second end, a body that runs between the first end and the second end, and a knot or fixed loop 35L disposed at the first end of the cord. The body of the cord passes through the knot or fixed loop so as to form (a) a loop portion 33 that follows a contour of the annulus and is positioned distally beyond the knot or fixed loop 35L and (b) a second portion 31 that runs between the knot or fixed loop and the second end. The knot or fixed loop 35L is configured so that the body of the cord can slide with respect to the knot or fixed loop 35L, and the anchors are distributed about the loop portion 33.

The cord 31/33 and the fixed loop 35L may be constructed as described above in connection with FIGS. 2-6. For example, the fixed loop could be secured by a surgeon's loop knot. In alternative embodiments, the fixed loop 35L depicted in FIG. 7 may be replaced with a knot (e.g., a noose knot, not shown), like the knot 35K described above in connection with FIG. 6. As described above in connection with FIG. 2-6, the anchors are implanted into the annulus or adjacent tissue so that immediately subsequent to implantation, each of the anchors will hold a respective part of the loop portion adjacent to the annulus. Although the embodiment illustrated in FIG. 7 has nine anchors 40A-40I, a different number of anchors may be used (e.g., between 6 and 24).

After implantation of the anchors, we wait for a bond to develop between the anchors and the annulus or adjacent tissue. This can take, for example, 4-8 weeks. Subsequent to the development of the bond, the second portion 31 of the cord is pulled in a proximal direction while holding the knot or fixed loop 35L in place to reduce the circumference of the annulus (e.g., as described above in connection with FIG. 3). Subsequent to the pulling, the cord 31/33 is fastened to prevent the annulus from expanding (e.g., as described above in connection with FIG. 4). This fastening may be accomplished, for example, by affixing a clip to the second portion adjacent to the knot or fixed loop, where the clip is positioned to prevent the loop portion of the cord from expanding.

The tricuspid valve has a septal leaflet, an anterior leaflet, and a posterior leaflet. The anchors 40A-40I may be distributed about the loop portion as depicted in FIG. 7 so that a first one of the anchors 40A is closest to the knot or fixed loop and a last one of the anchors 40I is furthest from the knot or fixed loop. Note that as used herein, "closest" and "furthest" are measured along the longitudinal direction of the cord. Thus, in the FIG. 7 embodiment, the anchor 40A is the anchor that is closest to the fixed loop 35L, the anchor 40B is the anchor that is second closest to the fixed loop 35L, the anchor 40C is the anchor that is third closest to the fixed loop 35L, etc. Finally, the anchor 40I is the anchor that is ninth closest to the fixed loop 35L, which means that it is the furthest from the fixed loop 35L. When the anchors 40A-40I are implanted, the first one of the anchors 40A is implanted into the septal leaflet or into a portion of the annulus to which the septal leaflet is attached, and the last one of the anchors 40I is implanted into the posterior leaflet or into a portion of the annulus to which the posterior leaflet is attached.

When the cord 31/33, the fixed loop 35L, and the anchors 40A-40I are arranged as described in the previous paragraph (e.g., as depicted in FIG. 7), and the second portion 31 of the cord is pulled in a proximal direction (while holding the knot or fixed loop 35L in place) to reduce the circumference of the annulus, the amount of force that is exerted on each of the anchors 40A-40I will not be uniform. To the contrary, due to the asymmetry of the lasso-like pulling arrangement, the forces exerted on certain anchors on the right side of FIG. 7 (e.g., 40E-H) will be larger than the forces exerted on the anchors on the upper left quadrant of FIG. 7 (e.g., 40B and 40C).

While this might appear to be problematic at first, it turns out that due to local variations in anatomy, anchors that are driven into the annulus closer to the boundary between the anterior and posterior leaflets (e.g., anchors 40E-H) often provide a more secure connection to the annulus as compared to anchors that are driven into the annulus near the top half of the septal leaflet (e.g., anchors 40B and 40C). And this anatomical difference matches up nicely with the differences in forces experienced by each of the anchors described above, because the anchors with the stronger connections will experience larger forces, while the anchors with the weaker connections will experience lower forces.

In addition, enlargement of the right side of the heart is typically unidirectional, with the right lateral wall of the heart moving laterally, while the septal wall remains relatively fixed. It is therefore advantageous to exert more pulling force on the right lateral side of the heart (which corresponds to the anterior and posterior leaflets depicted in FIG. 7) to move the right lateral side of the heart back towards its original position. This provides yet another reason why the arrangement described above in connection with FIG. 7 is advantageous.

Moreover, the prior art FIG. 1 configuration relies on two sections of cord that extend from the loop portion to achieve tightening of the annulus, while all of the embodiments described above in connection with FIGS. 2-7 require only a single section of cord that extends from the loop portion to tighten the annulus. This reduction from two sections to one section can advantageously simplify the design of the fasteners that fasten the cord in its reduced-diameter state, simplify the design of mechanisms for cutting the cord after the cord has been fastened, and reduce the diameter of the catheters that are used to install the device in the patient. In addition, the embodiments described above in connection with FIGS. 2-7 all have a closed loop with a single cord extending from the adjustment point. This configuration dramatically reduces the risk of yanking out an individual anchor when pulling on the second portion of the cord (in contrast to the prior art FIG. 1 configuration, where pulling to hard on one of the proximal sections 14A and 14B of the cord can yank out the anchor 16 that is closest to that proximal section.

Note that while the FIG. 2-6 the embodiments are described above in the context of installing an implant on the annulus of a cardiac valve (e.g., the mitral valve or the tricuspid valve) or into adjacent tissue, the same apparatus can also be used to constrict other anatomic passages or other anatomic annuli (with appropriate modifications for scaling to size as dictated by the relevant anatomy). In these other anatomic contexts, the anchors would be implanted into the anatomic passage or into tissue adjacent to the anatomic passage. After waiting for injury points and/or tissue healing to strengthen the bond between the implant and the tissue, pulling the second portion 31 of the cord 30 while holding the fixed loop 35L or knot 35K in place (e.g., using a push tube) will reduce the diameter of the anatomic passage.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for resizing an annulus of a valve of a heart of a subject, the annulus having a circumference, the apparatus comprising:
   a cord:
      having a first end, a second end, and a body that runs between the first end and the second end, and defining an eye at the first end of the cord, wherein the body of the cord passes through the eye so as to form the cord into a lasso-like arrangement in which (a) a loop portion of the body of the cord is positioned distally beyond the eye and (b) a second portion of the body of the cord runs between the eye and the second end, and wherein the eye is configured so that the body of the cord can slide bidirectionally through the eye;

at least four anchors slidably threaded onto the body of the cord so as to be distributed about the loop portion;

a delivery system, configured to transluminally advance the cord to the heart and anchor the loop portion about the annulus by driving the anchors into tissue of the annulus while the second end remains outside of the subject;

a clip, larger than the eye; and a pusher, configured to (i) contract the loop portion by pushing distally while the body of the cord is pulled proximally through the eye, and (ii) affix the clip to the second portion, adjacent to the eye, such that the eye obstructs the clip from passing distally through the eye, thereby preventing re-expansion of the loop portion.

2. The apparatus of claim 1, further comprising a sleeve of material that accepts tissue ingrowth disposed over the loop portion.

3. The apparatus of claim 2, wherein each of the at least four anchors is configured to hold a respective part of the loop portion adjacent to the annulus by holding a corresponding part of the sleeve to the annulus.

4. The apparatus of claim 2, wherein the sleeve comprises a first of multiple sleeves, the multiple sleeves and the at least four anchors distributed alternatingly about the loop portion.

5. The apparatus according to claim 2, wherein the sleeve comprises a lining that resists tissue ingrowth.

6. The apparatus of claim 1, wherein the eye is defined by a fixed loop that is secured by a surgeon's loop knot.

7. The apparatus of claim 1, wherein the eye is defined by a noose knot.

8. The apparatus of claim 1, wherein each of the at least four anchors includes a pointy front end and a back end, and a slot that runs in a front-to-back direction.

9. The apparatus of claim 8, wherein the slot is a linear slot.

10. The apparatus according to claim 1, further comprising a pouch configured to be temporarily implanted at a subcutaneous site and to house the second end of the cord such that the second portion of the cord extends between the pouch at the subcutaneous site and the loop portion at the annulus.

11. The apparatus according to claim 1, wherein the second portion is 25-100 cm long.

12. The apparatus according to claim 1, wherein the annulus is a mitral annulus of a mitral valve, and the delivery system is configured to transluminally advance the loop portion to the mitral valve and anchor the loop portion about the mitral annulus.

13. The apparatus according to claim 1, wherein the annulus is a tricuspid annulus of a tricuspid valve, and the delivery system is configured to transluminally advance the loop portion to the tricuspid valve and anchor the loop portion about the tricuspid annulus.

14. A method for resizing an annulus of a valve of a heart of a subject, the annulus having a circumference, the method comprising:

using a delivery system to transluminally deliver to the heart:
  a cord:
    having a first end, a second end, and a body that runs between the first end and the second end, and
    defining an eye at the first end of the cord, wherein the body of the cord passes through the eye so as to form the cord into a lasso-like arrangement in which the body of the cord defines a loop portion and can slide bidirectionally through the eye, and
  at least four anchors slidably threaded onto the body of the cord so as to be distributed about the loop portion; and implanting the anchors into the annulus so that the anchors engage tissue of the annulus to hold the loop portion adjacent to the annulus, with the loop portion following a contour of the annulus, while the second end remains outside of the subject; and using a pusher to (i) contract the loop portion by pushing distally while the body of the cord is pulled proximally through the eye, and (ii) affix a clip that is larger than the eye to a second portion of the body of the cord, which runs between the eye and the second end, adjacent to the eye, such that the eye obstructs the clip from passing distally through the eye, thereby preventing re-expansion of the loop portion.

15. The method of claim 14, further comprising:

prior to using the pusher to (i) contract the loop portion by pushing distally while the body of the cord is pulled proximally through the eye, and (ii) affix the clip to the second portion of the body of the cord waiting for a bond to develop between the anchors and the annulus.

16. The method of claim 14, wherein the valve is a tricuspid valve and has a septal leaflet, an anterior leaflet, and a posterior leaflet, wherein the anchors are distributed about the loop portion so that a first one of the anchors is closest to the eye and a last one of the anchors is furthest from the eye, and wherein when the anchors are implanted, (a) the first one of the anchors is implanted into a portion of the annulus to which the septal leaflet is attached and (b) the last one of the anchors is implanted into a portion of the annulus to which the posterior leaflet is attached.

\* \* \* \* \*